United States Patent [19]

Yaguchi et al.

[11] Patent Number: 5,082,717

[45] Date of Patent: Jan. 21, 1992

[54] STYRENE-BASED RESIN COMPOSITE MATERIAL

[75] Inventors: Atsunori Yaguchi, Chiba; Keisuke Funaki, Ichihara, both of Japan

[73] Assignee: Idemitsu Petrochemical Co., Ltd., Tokyo, Japan

[21] Appl. No.: 443,937

[22] Filed: Nov. 30, 1989

[30] Foreign Application Priority Data

Dec. 16, 1988 [JP] Japan ................ 63-316168
Dec. 16, 1988 [JP] Japan ................ 63-316169
Jan. 31, 1989 [JP] Japan ................ 1-019497

[51] Int. Cl.$^5$ .............. B32B 27/28; C08J 7/04; B41J 31/05; C09D 185/02
[52] U.S. Cl. .................... 428/207; 428/521; 428/695; 428/900; 428/480; 428/447; 428/1; 428/412; 428/419; 428/516; 428/518; 428/421; 428/494; 428/495; 528/168; 526/160
[58] Field of Search ............ 428/207, 480, 913, 914, 428/521

[56] References Cited

U.S. PATENT DOCUMENTS

| | | | |
|---|---|---|---|
| 4,103,066 | 7/1978 | Brooks et al. | 428/914 |
| 4,675,233 | 6/1987 | Nakahara et al. | |
| 4,680,353 | 7/1987 | Ishihara et al. | |
| 4,721,703 | 1/1988 | Kobayashi et al. | 428/913 |
| 4,812,360 | 3/1989 | Utsumi | |

FOREIGN PATENT DOCUMENTS

| | | | |
|---|---|---|---|
| 337316 | 10/1989 | European Pat. Off. | 428/412 |
| 217194/1985 | 10/1985 | Japan | |
| 111719/1987 | 5/1987 | Japan | |

*Primary Examiner*—P. C. Sluby
*Attorney, Agent, or Firm*—Frishauf, Holtz, Goodman & Woodward

[57] ABSTRACT

Disclosed are a styrene-based resin composite material in which a layer composed mainly of a curable phosphazene compound is formed on the surface of a molding material of a styrene-based polymer having a mainly syndiotactic configuration or a composition thereof, and also an ink ribbon in which an ink layer is provided on one side of a film of the above polymer of a composition thereof and a heat resistant lubricating layer composed mainly of the curable phosphazene compound provided on the side opposite thereto, and also a magnetic recording medium characterized in that a magnetic layer containing the curable phosphazene compound as a binder on a support composed of the above polymer or a composition thereof, a over coated layer of a magnetic recording medium which contains the curable phosphazene compound and a lubricating layer of a magnetic recording medium which contains the curable phosphazene compound.

5 Claims, No Drawings

STYRENE-BASED RESIN COMPOSITE MATERIAL

BACKGROUND OF THE INVENTION

1. Field of the Invention

This invention relates to a styrene-based resin composite material. More particularly, it relates to a styrene-based resin composite material in which a hard coating layer having high hardness and excellent adhesiveness is formed on the surface of a molding material comprising a styrene-based polymer having a syndiotactic configuration or its composition, a thermal transfer ink tape formed with a base film prepared by stretch-formed material with a styrene-based polymer or a composite composed with a lubricating heat resistant layer of curable phosphazene compound, and a magnetic recording medium having a curable phosphazene compound formed with a binder of magnetic layer and a lubricating layer on a support composed of a styrene-based polymer thereof.

2. Description of the Related Arts

A styrene-based polymer having a syndiotactic configuration, which is a crystalline polymer with excellent mechanical strength, heat resistance, chemical resistance, etc. compared with a styrene-based polymer having an atactic configuration so that can be used for various moldings, base films, etc. On applying these base film to the various usage, various hard-coating treatment in accordance with the surface hardness, lubricity and resistance to solvents of this material which is expected to each usage, has been considered.

Hard coating materials known heretofore are acrylic and silicone types. Among these, the acrylic type hard coating material can rather easily form a coating layer by irradiation of ultraviolet rays, etc. compared with others, but is insufficient in terms of adhesiveness and hardness. On the other hand, the silicone type hard coating material can form a coating layer with good adhesiveness by applying a primer treatment. However, it requires a longer curing time for heat treatment and has a migration problem, therefore, is also inadequate.

Furthermore, these hard coating materials have insufficient adhesiveness to a molded material comprising a styrene-based polymer having a syndiotactic configuration or its composition.

On the other hand, magnetic recording media such as a magnetic tape for video recorder, a magnetic tape for audio recording, a magnetic tape for computers, a magnetic disc, a magnetic drum, and a magnetic card, for which demand has been increasing in recent years, are prepared by coating a magnetic composition containing magnetic materials such as $\gamma$-iron oxide onto a support such as a plastic film, disc, and card to form a magnetic layer thereon.

As the support for this purpose, a polyethyleneterephthalate (PET) film has heretofore been used, but it is insufficient in heat resistance, thus information in the medium cannot sometimes be output due to deformation of the support.

Furthermore, one of the requirements for the support for a tape is high mechanical strength. Increasing the reliability of running systems for a tape of a tape recorder, reducing the total film thickness of the tape, and accompanying higher density and narrower recording tracks, improved mechanical strength is strongly required for a tape support. Considering running properties and durability, it is particularly important that the bending strength of the tape itself be sufficient, i.e. characteristics regarding elasticities and surface hardness to decrease friction of the support itself. However, those which use the conventional PET films as a support are inadequate in terms of these characteristics and improvement thereof has been desired.

Also, a binder is added to the magnetic composition in order to adhere the magnetic material to the support. As the binder, acrylic type resins, ester type resins, epoxy type resins, urethane type resins, isocyanate type resins or silicone type resins have heretofore been known, but a magnetic layer formed by adding these binders has insufficient adhesiveness with the support, and durability and wear-resistance are also inadequate. Furthermore, it involves the defect of inferior solvent resistance.

As well as magnetic tape, there are ink ribbons which utilize the conventional polyethylene telephthalate (PET) film as a support. An ink ribbon is recognized the improvement of a characteristic from the conventional heat fusion type to the sublimation type corresponded to color printing, and the usage are expected to develop not only to the monochronous letter printing, but also Facsimile, Printing correction, a direct printing from TV and VIDEO recorders.

An ink ribbon is composed of three layers of an support (base film), ink layer and back coated layer (lublicating heat resistant layer). A back coated layer is formed in order to improve lubricity of a ribbon and prevent a damage from heat of a thermal head. Silicone type resin mainly has been used on the back coated layer, but the migration due to insufficient hardening, bad printing and bad coating on an ink layer on preparing a ribbon occurred.

The present inventors have intensively studied the subject to develop a material which can form a film or a binder layer containing magnetic materials with excellent adhesiveness, hardness, solvent resistance, wear-resistance, lubricity, etc., with one coating on a molding material or a base film comprising the above styrene-based polymer having a syndiotactic configuration.

SUMMARY OF THE INVENTION

The object of the present invention is to provide a styrene-based resin composite material which forms a coating film with excellent adhesiveness, hardness, solvent resistance, lubricity, heat resistance, etc., onto a molding material comprising a styrene-based polymer having a syndiotactic configuration.

Another object of the present invention is to provide an ink ribbon on which an ink layer is formed on one side of a base film comprising the above styrene-based polymer or its composition, and a layer with excellent heat resistance and lubricating qualities is formed on the opposite side.

A further object of the present invention is to provide a magnetic recording medium in which a layer is formed on a support comprising the above styrene-based polymer or its composition, that contains a lubricating layer with excellent adhesiveness, and a magnetic material, which is adhered to said support and has excellent mechanical strength.

That is, the present invention provides a styrene-based resin composite material which comprises a molding material of a styrene-based polymer having a syndiotactic configuration or its composition (the composition containing the styrene-based polymer) and a layer mainly comprising a curable phosphazene compound formed on a surface of the molding material. The present invention also provides an ink ribbon comprising a base film prepared by stretching a styrene-based polymer having a syndiotactic configuration and an ink layer on the base film, characterized in that a heat resistant and lubricating layer composed mainly of a curable phosphazene compound is formed on the base film at the opposite side to the ink layer. Moreover, the present invention provides a magnetic recording medium comprising a support composed mainly of a styrene-based polymer having a syndiotactic configuration, a magnetic layer containing a curable phosphazene compound as a binder on the support, a back coated layer containing a curable phosphazene compound (lubricating layer) on the support at the opposite side of the magnetic layer and a magnetic over coated layer containing a curable phosphazene compound on the magnetic layer.

The following usages are expected on the styrene based resin composite material forming a hard coated layer which contains a curable phosphazene resin. These are a touch panel, a liquid crystal panel and a photo mask film etc. in an electronics field; facsimile, pre-paid card in office automation (OA) field; lens of head lamp, cover for meters, wheel cover in an automobile field; lens, plastic mold, pattern paper in preparing vinyl chloride leather sheet, pattern paper in processing ceramics green sheet in other fields.

DESCRIPTION OF PREFERRED EMBODIMENTS

In the present invention, a styrene-based polymer which is used as the raw material of a molding material, a base film or a support, has a syndiotactic configuration. Here, the syndiotactic configuration means that the stereostructure is a syndiotactic configuration, i.e., the stereostructure in which phenyl groups or substituted phenyl groups are located as side chains alternately in opposite directions relative to the main chain consisting of carbon-carbon bonds. The tacticity is quantitatively determined by the nuclear magnetic resonance method using a carbon isotope ($^{13}$C-NMR) method. The tacticity, as determined by the $^{13}$C-NMR method, can be represented in terms of the proportions of structural units continuously connected to each other, i.e., a diad in which two structural units are connected to each other, a tried in which three structural units are connected to each other, or pentad in which five structural units are connected to each other. The styrene-based polymers having such a syndiotactic configuration such that the proportion of racemic diad is at least 75% and preferably at least 85%, or the proportion of racemic pentad is at least 30% and preferably at least 50% syndiotacticity. The styrene-based polymers having a syndiotactic configuration of the present invention include polystyrene, poly(alkylstyrene), poly(halogenated styrene), poly(alkoxystyrene), poly(vinyl benzoate ester) and mixtures thereof, and copolymers containing them as main components. In the case of styrene-based polymers with low syndiotacticity, the resulting materials have substantially the same physical properties, such as heat resistance, as conventional polystyrene. The above poly(alkylstyrene) includes poly(methylstyrene), poly(ethylstyrene), poly(isopropylstyrene), poly(tert.-butylstyrene), etc., and the poly(halogenated styrene) includes poly(chlorostyrene), poly(bromostyrene), poly(fluorostyrene), etc. The poly(alkoxystyrene) also includes poly(methoxystyrene), poly(ethoxystyrene), etc. The most preferred styrene-based polymers are polystyrene, poly(p-methylstyrene), poly(m-methylstyrene), poly(tert.-butylstyrene), poly(p-chlorostyrene), poly(m-chlorostyrene), poly(p-fluorostyrene), and a copolymer of styrene and p-methylstyrene (Japanese Patent Application Laid-Open No. 187708/1987).

The molecular weight of the styrene-based polymer used in the present invention is not critical, but is preferably at least 10,000, and most preferably at least 50,000 of a weight average molecular weight. Stretching those having a weight average molecular weight of less than 10,000 cannot be done sufficiently. The molecular weight distribution is not critical, and the styrene-based polymers in various ranges of molecular weight distribution can be applied. Styrene-based polymers having a syndiotactic configuration have a melting point of 160° to 310° C., and thus are much superior in heat resistance to conventional styrene-based polymers having an atactic configuration.

The styrene-based polymers having a syndiotactic configuration can be produced by polymerizing styrene-based monomers (corresponding to the above styrene-based polymers) using a catalyst comprising a titanium compound and a water and a condensate of trialkylauminum in, for example, an inert hydrocarbon solvent, or in the absence of a solvent (Japanese Patent Application Laid-Open No. 187708/1987).

In the present invention, styrene-based polymers having syndiotactic configuration are used as mentioned above, and if necessary, a composition can be made by adding various additives such as a thermoplastic resin, rubber, an inorganic filler, an antioxidant, a nucleating agent, and a plasticizer, a compatibilizer, a colorant, an antistatic agent, depending on moldability, stretching properties and other properties to be obtained.

Thermoplastic resins which can be used include, for example, styrene-based polymers such as polystyrene having an atactic structure, polystyrene having an isotactic structure, an AS resin, an ABS rein, etc., polyesters such as polyethylene terephthalate; polycarbonates; polyethers such as polyphenylene oxide, polysulfone, and polyethersulfone; condensation polymers such as polyamide, polyphenylene sulfide (PPS) and polyoxymethylene; acryl-based polymers such as polyacrylic acid, polyacrylate ester and polymethyl methacrylate; polyolefins such as polyethylene, polypropylene, polybutene, poly(4-methyl-pentene-1), and an ethylene-propylene copolymer; and halogenated vinyl polymer such as polyvinyl chloride, polyvinylidene chloride, and polyvinylidene fluoride.

Although various rubbers can be used, rubber-like copolymers containing a styrene-based compound as one component are most preferred. Examples are rubbers obtained by partially or fully hydrogenating the butadiene portion of a styrene-butadiene block copolymer (SEBS), styrene-butadiene copolymer rubber (SBR), methyl acrylate-butadiene-styrene copolymer rubber, acrylonitrile-butadiene-styrene copolymer rubber (ABS rubber), acrylonitrile-alkyl acrylate-butadien-styrene copolymer rubber (AABS), methyl methacrylate-alkyl acrylate-styrene copolymer rubber (MAS), and methyl methacrylate-alkyl acrylate-butadiene-styrene copolymer rubber (MABS). These rubber-like copolymers, containing a styrene-based compound as one component, have good dispersibility in styrene-based polymers having a mainly syndiotatic configuration, because they have the styrene unit and, therefore, can remarkably improve physical properties.

Other rubbers which can be used include natural rubber, polybutadiene, polyisoprene, polyisobutylene, neoprene, ethylene-propylene copolymer rubber, polysulfide rubber, thiokol rubber, acrylic rubber, urethane rubber, silicone rubber, epichlorohydrin rubber, polyether ester rubber, and polyester ester rubber, etc.

The shape of the inorganic filler is not critical and may be fibrous, or granular of a powder. Examples of fibrous inorganic fillers are glass fibers, carbon fibers, and alumina fibers. Examples of granular or powder inorganic filler are talc, carbon black, graphite, titanium dioxide, silica, mica, calcium carbonate, calcium sulfate, barium carbonate, magnesium carbonate, magnesium sulfate, barium sulfate, oxysulfate, tin oxide, alumina, kaolin, silicon carbide, and metal powder.

If the molding material is a film, these inorganic fillers have a large effect on the film surface according to the form, especially in the case of a thin film, in terms of the diameter of the particle etc., so they are usually selected so that the particle diameter is smaller than 1/5, preferably smaller than 1/10 of the thickness of the film, and the desired surface-properties and physical properties can be obtained according to the object. Two or more kinds of inorganic fillers can be used in combination.

Although various antioxidants can be used, phosphorus-based antioxidants such as monophosphites, e.g., tris(2,4-di-tert-butylphenyl) phosphite and tris(mono-or di-nonyl-phenyl) phosphite, and diphosphites, and phenol-based anti-oxidants are preferably used. Preferred diphosphites to be used are the phosphorous compounds represented by the formula:

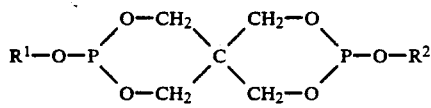

(wherein $R^1$ and $R^2$ are each of an alkyl group having 1 to 20 carbon atoms, a cycloalkyl group having 3 to 20 carbon atoms, or an aryl group having 60 to 20 carbon atoms).

Typical examples of the phosphorus compounds represented by the above formula are distearylpentaerythritol diphosphite, dioctylpentaerythritol diphophite, diphenylpentaerythritol diphosphite, bis(2,4-tert.-butylphenyl) pentaerythritol diphosphite, bis(2,6-di-tert.-butyl-4-methylphenyl)-pentaerythritol diphosphite, and dicyclohexylpetaerythritol diphosphite.

Various kinds of known compounds can be used as the phenolic antioxidant. Typical examples of them are 2,6-di-tert.-butyl-4-methylphenol, 2,6-diphenyl-4-methoxylphenol, 2,2'-methylene-bis(6-tert.-butyl-4-methylphenol), 2,2'-methylenebis[4-methyl-6-(α-methylcyclohexyl) phenol], 1,1-bis(5-tert.-butyl-4-hydroxy-2-methylphenyl) butane, 2,2'-methylenebis(4-methyl-6-cyclohexylphenol), 2,2-methylenebis(4-methyl-6-nonylphenol), 1,1,3-tris(5-tert.-butyl-4-hydroxy-2-methylphenyl) butane, 2,2-bis(5-tert.-butyl-4-hydroxy-2-methylphenyl)-4-n-dodecyl-mercaptobutane, ethyleneglycol-bis[3,3-bis(tert.-butyl-4-hydroxyphenyl) butylate], 1,1-bis(3,5-dimethyl-2-hydroxyphenyl)-3-(n-dodecylthio) butane, 4,4-thiobis(6-tert.-butyl-3-methylphenol), 1,3,5-tris(3,5-di-tert.-butyl-4-hydroxybenzyl)-2,4,6-trimethylbenzene, 2,2-bis(3,5-di-tert.-butyl-4-hydroxybenzyl)-malonic acid dioctadecyl ester, n-octadecyl-3-(4-hydroxy-3,5-di-tert.-butylphenyl) propionate, and tetrakis [methylene(3,5-di-tert.-butyl-4-hydroxyhydrocinnamate)] methane.

The above antioxidant is compounded in the amount of 0.001 to 2 parts by weight, preferably 0.001 to 1 part by weight per 100 parts by weight of the styrene-based polymer having syndiotactic configuration mentioned before. If the amount of the antioxidant compound is less than 0.001 parts by weight, sufficient effects can not be obtained because the molecular weight decreases steeply. On the other hand, if it is more than 2 parts by weight, the mechanical strength is adversely affected.

In the present invention, a layer composed mainly of a curable phosphazene compound is formed on the surface of the moldings comprising the above styrene-based polymer or its composition. The form of the molding materials before forming the layer, molding method and degree of crystallization are not particularly limited, and they may be optionally determined depending on the characteristics required of the molding materials to be formed. For example, the form may be a film, a sheet, fiber, or a container such as bottle, and the molding method that may be applied can be extrusion molding, injection molding, thermoforming, inflation molding, spinning, stretching, molding, etc. Furthermore, the crystallinity is not particularly limited, and it may be either crystalline or amorphous. If necessary, those which are subjected to heat treatment after molding may also be used.

In the present invention, in addition to a stretched film obtained from the styrene-based polymer or its composition and a stretched film which is subjected to heat treatment, a container obtained by blow molding, a fiber obtained by melt spinning, a nonwoven fabric, a sheet obtained by extrusion molding using a T-die, can be applied.

A molding material having a sheet or cylindrical shape can be formed by melting the above styrene-based polymer or its composition, putting the molten polymer into a die such as a T-die or circular die and then extruding with an extruder. During the operation, the degree of crystallization can be controlled by varying the cooling method or conditions. Furthermore, bottle-like shaped moldings can be formed by blow molding a material extruded from the circular die.

Furthermore, a molding having a complicated shape can be obtained by further molding a sheet or tube obtained by the above procedure, such as heat molding, or by directly performing injection molding. On carrying out the above molding, it is usual for the molten material to be molded to a predetermined shape by various molding machines, but molding may be carried out in a soft condition without melting the material. The melting temperature of the material is, if the styrene-based polymer is polystyrene, generally 260° to 350° C., and preferably 280° to 3330° C. If the temperature is too high, the molding material is decomposed.

When the molding material is the base film of an ink ribbon, a thickness of the raw sheet may be freely selected, but usually it can be freely determined in the range of 5 mm or less, preferably in the range of 3 mm to 20 μm. If the thickness exceeds 5 mm, crystallization at the inner portion goes on so that the sheet may sometimes become difficult to stretch. The crystallinity of the raw sheet (or film) is 30% or less, preferably 10 to 25%, and more preferably 10 to 20%.

For cooling the sheet after extrusion, the temperature of the coolant should be set at 0° to 130° C., preferably 20 to 100° C., and more preferably 50° C. or lower. If the temperature of the coolant is too high, cooling becomes slow and a crystallinity increases in excess and the sheet becomes difficult to stretch.

The equipment in which coolant temperature is low is uneconomical in productivity in addition to the higher cost of equipment.

For the stretching treatment of the raw sheet, it is usually subjected to uniaxial or biaxial stretching at temperatures from the glass transition temperature to the melting point of the material. The stretching temperature is from the glass transition temperature to the melting point, and it is preferably from the glass transition temperature to a temperature of 30° C. less than a melting point. Regarding the draw ratio, in the case of the uniaxial stretching, stretching should be carried out twice or more, preferably three times or more, more preferably three to ten times to a stretching direction. In the case of the biaxial stretching, stretching should be carried out one and a half times or more, preferably twice or more in the respective stretching direction (biaxial direction). If the draw ratio is too small, the physical properties of the resulting film are not suitable for the base film of the present invention. In the case of the above biaxial stretching, stretching may be carried out simultaneously in the mechanical direction (MD) and the transverse direction (TD), but it may be carried out sequentially in any order.

In the present invention, when biaxial stretching is carried out particularly other than the above method, a biaxial stretched film can be obtained by directly inflation molding the above material without making the raw sheet or premolding. When inflation molding is carried out, it is effective to increase the resin temperature at fusion until it is 20° C. or higher than the melting point to prevent melt fracture, surface roughening, etc. However, if it is too high, thermal decomposition occurs so it should preferably be set within the range of 180° to 330° C. The stretching temperature may be 10° C. lower than the melting temperature. For inflation molding, if the blown up ratio is small, monoaxial stretching is also possible.

The stretched film obtained as mentioned above, has a thickness of 1 to 50 μm, preferably 2 to 30 μm, and particularly preferably 3.5 to 20 μm, when it is used as the base film of the present invention.

After the above stretching, heat treatment (annealing) may be carried out. Heat treatment may be carried out at the temperature range of a glass transition temperature to melting point with fixed ends of the film. Heat resistance, dimensional stability and chemical resistance of the film are remarkably improved by the heat treatment.

A support for a magnetic recording medium can be obtained by molding the styrene-based polymer or a composition containing the said polymer and, if necessary, various kinds of additives are added to such a molded product as a film, tape, disc, or card. The thickness of these supports can be freely selected depending on the purpose, but when the support is in a film stage, it usually has a thickness of 1 to 100 μm, and preferably 3 to 80 μm. This film may be subjected to or may not be subjected to stretching molding. The stretching molded material containing a large amount of an inorganic filler, incompatible resin or rubber is not preferred. On the other hand, when it is used without being subjected to stretching molding, an inorganic filler, resin and rubber are sufficiently compounded taking into consideration of mechanical propertied and heat resistance.

The stretched film to be the base film of magnetic recording medium can be prepared by the same manner as in the base film of an ink ribbon described above. Time and temperature of the heat treatment can be freely selected in view of the draw ratio, thickness and composition, or usage, physical properties of the stretched material. It is usually carried out at the glass transition temperature to the melting point for 1 second and 100 hours, preferably at a temperature of 20° C., higher than the glass transition temperature to a temperature of 5° C. lower than the melting point for from 5 second to 30 minutes. If it is less than the glass transition temperature, heat treatment has no effect, and if it exceeds the melting point, the film melts partially or entirely during the heat treatment.

The draw ratio during stretching is preferably three times or more in terms of the area ratio (that is, an area ratio of the film after stretching to that of the raw sheet), more preferably six times or more in view of the mechanical properties of the film.

In addition, the raw sheet obtained by cooling may be any shape, a cylinder or plain, and may be stretched by a gas (that is, inflation, blowing molding) or tenter simultaneously or in sequentially.

When a circular die is used, the tube may be stretched immediately after melting at the glass transition temperature or higher to the melting point.

To thus formed various molding materials, a hard coating layer composed mainly of a curable phosphazene compound is formed in the present invention.

The curable phosphazene compound to be used in the present invention is a compound having a recurring unit of

(wherein a and b are real numbers satisfying $a > 0$ and $b \geq 0$, and $a + b = 2$, A represents a group that can be cured by polymerization, and B represents a group that cannot be cured by polymerization), and having a polymerization degree of three or more.

In the present invention, the hard coating layer on the surface of the molding material is formed by curing a coating material containing, as a main component, a phosphazene compound having the recurring unit represented by the formula (I) as mentioned above. Here, the formula (I) dose not show a single compound but a represents the average value of a mixture comprising several kinds of compounds. Thus, a and b representing each group is not necessarily limited to integers but also to real numbers containing decimals. In addition, regarding the degree of polymerization, it contains not only integers in the range of three or more, but also real numbers containing decimals.

The phosphazene compound having the recurring unit of the above formula (I) may include various ones according to the kinds of each substituent.

In the formula, A represents a group that can be cured by polymerization, which means a functional group which is cured by the reaction caused by irradiation of a UV-ray, visible ray or electron beam, use of a chemical curing agent or heating, and it usually refers to a group having a reactive double bond. There are various groups having reactive double bonds, for example, functional groups containing an acryloyl group, methacryloyl group, an allyl group or vinyl group.

The above functional groups containing the acryloyl group or the methacryloyl group may include an acryloyloxy group, a methyacryloyloxy group or that represented by the formula:

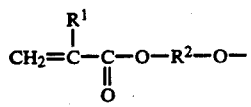
(II)

(wherein $R^1$ represents a hydrogen atom or a methyl group, and $R^2$ represents a straight or a branched alkylene group having 1 to 12 (preferably 1 to 5) carbon atoms).

Specific examples of the group represented by the above formula (II) may include a residual group eliminating hydrogen atom from a hydroxyl group of methacrylates such as 2-hydroxyethylmethacrylate, 2-hydroxypropylmethacrylate, 3-hydroxypropylmethacrylate, 2-hydroxybutylmethacrylate, 3-hydroxybutylmethacrylate, 4-hydroxybutylmethacrylate, 5-hydroxypentylmethacrylate, 6-hydroxy-3-methylhexylmethacrylate, 5-hydroxyhexylmethacrylate, 3-hydroxy-2-t-butylpropylmethacrylate, 3-hydroxy-2, 2-dimethylhexylmethacrylate, 3-hydroxy-2-methyl-2-ethylpropylmethacrylate and 12-hydroxydodecylmethacrylate; and a residual group eliminating hydrogen atoms from a hydroxyl group of acrylates such as 2-hydro-xyethylacrylate, 2-hydroxypropylacrylate, 3-hydroxypropylacrylate, 2-hydroxybutylacrylate, 3-hydroxybutylacrylate, 4-hydroxybutylacrylate, 5-hydroxypentylacrylate, 6-hydroxy-3-methylhexylacrylate, 5-hydroxyhexylacrylate, 3-hydroxy-2-t-butylpropylacrylate, 3-hydroxy-2,2-dimethylhexylacrylate, 3-hydroxy-2-methyl-2-ethylpropylacrylate and 12-hydroxy-dodecylacrylate. Particularly preferred groups are 2-hydroxy-ethylmethacrylate residue and 2-hydroxyethylacrylate residue.

In addition to the above functional groups containing the acryloyl group or methacryloyl group of the formula (II), there is a functional group represented by the formula:

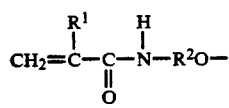
(III)

(wherein $R^1$ and $R^2$ have the same meanings as defined above), that is, a residual group eliminating hydrogen atoms from the hydroxyl group of hydroxyalkyl-substituted (meth)acrylamide, and further a functional group represented by the formula:

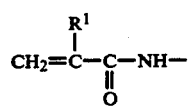
(IV)

(wherein $R^1$ has the same meaning as defined above), that is a residual group eliminating hydrogen atoms from the amino group of acrylamide or methacrylamide.

Furthermore, a functional group containing an allyl group may include an allyloxy group ($CH_2=CH-CH_2O-$) in addition to the allyl group itself. However, it is not limited only to the above allyloxy group and may widely include the functional groups represented by the formula:

(V)

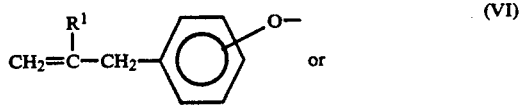
(VI)

or

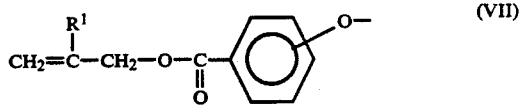
(VII)

(wherein $R^1$ and $R^2$ each have the same meanings as defined above, and $R^3$ and $R^4$ each independently represent hydrogen atoms or an alkyl group having 1 to 4 carbon atoms), that is, residual groups eliminating hydrogen atoms from a hydroxyl group of an allyl compound having a hydroxyl group. Specific examples of the functional groups represented by the formulae (V) to (VII) may include residues eliminating hydrogen atoms from hydroxyl group of allyl compounds represented by the formulae:

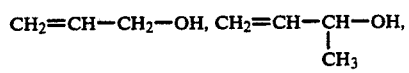

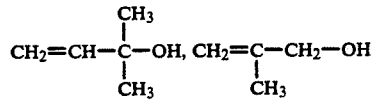

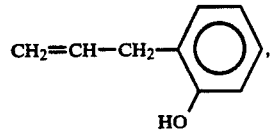

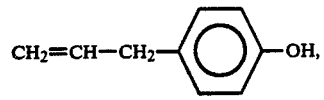

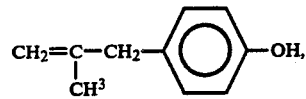

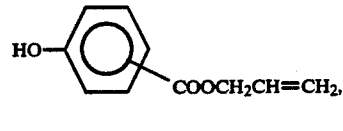

On the other hand, B in the formula (I) shows a group represented by the formula:

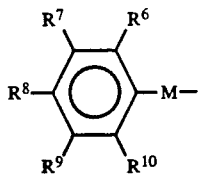

Here, in the formula (VIII), M represents an oxygen atom, a sulfur atom or an imino group, $R^5$ represents an alkyl group having 1 to 18 carbon atoms or a halogenated alkyl group having 1 to 18 carbon atoms. More specifically, they may include an alkoxy group such as methoxy group, ethoxy group, propoxy group, butoxy group, penthyloxy group, hexyloxy group, heptyloxy group, or octyloxy group; the above alkoxy group is substituted by a halogen atom (e.g. fluorine, chlorine, bromine, etc.); an alkylthio group such as methylthio group, ethylthio group, propylthio group, butylthio group, pentylthio group, heptylthio group, or octylthio group, the above alkylthio group is substituted by a halogen atom (e.g. fluorine, chlorine, and bromine); an alkylimino group such as methylimino group, ethylimino group, propylimino group, butylimino group, pentylimino group, hexylimino group, heptylimino group, or octylimino group; the above alkylimino group is substituted by a halogen atom (e.g. fluorine, chloride, and bromine) and the like. In addition M in the formula (IX) is the same as that mentioned above, and $R^6$ to $R^{10}$ each independently represent hydrogen atom, a halogen atom, an alkyl group having 1 to 4 carbon atoms or a halogenated alkyl group having 1 to 4 carbon atoms. Groups in the formula (IX) may include, for example, phenoxy group, thiophenyl group, a halogenated phenoxyl group (2,4,6-tribromophenoxy group, 4-bromophenoxy group, 2-chlorophenoxy group, 2,4-dichlorophenoxy group, etc.), a halogenated thiophyenyl group (4-chlorophenylthio group, etc.), or a residual group eliminating hydrogen atom from amino group of aniline or a halogenated aniline (2-chloroanilino, 2,4-dichloroaniline, or 2,4,6-tribromoaniline, etc.).

Regarding a and b in formula (I) above, they may be real numbers satisfying the relations of $0 < a \leq 2$ and $0 \leq b < 2$, and $a+b=2$, but preferably $0.6 \leq a \leq 2$ and $0 \leq b \leq 1.4$.

The substituent A is a group in which the hard coat layer composed mainly of the phosphazene compound of the formula (I) cures, and the substituent B is a group having the function of controlling physical properties of the cured material and also controlling the polymerization properties. By optionally selecting a and b, various physical properties of the composite material having a hard coat layer composed mainly of the phosphazene compound have been regulated accordingly.

However, because the compound wherein $a=0$ does not cure, such a phosphazene compound is excluded from the component of the hard coat layer of the present invention. Conversely, the compound wherein $a=2$ and $b=0$, i.e. the phosphazene compound having recurring unit is represented by the formula:

and can be utilized as a component of the hard coating layer of the present invention.

The phosphazene compound to be used in the present invention has the above recurring unit represented by the formula (I), and a polymerization degree of three or more, preferably in the range of 3 to 10,000, more preferably in the range of 3 to 18, in particular three or four or optimum mixtures thereof. The recurring unit represented by the formula (I) may be bonded (polymerized) linearly, but is preferably bonded (polymerized) in cyclization.

Examples of such phosphazene compounds may include those shown below.

Cyclic compound represented by the formula:

Cyclic compound represented by the formula:

Cyclic compound represented by the formula:

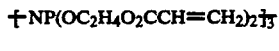

Cyclic compound represented by the formula:

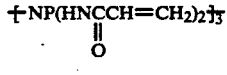

Cyclic compound represented by the formula:

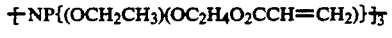

Cyclic compound represented by the formula:

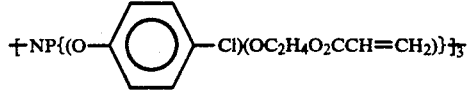

Cyclic compound represented by the formula:

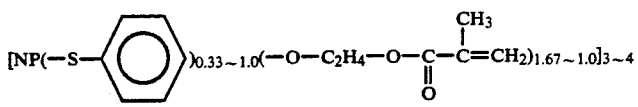

Cyclic compound represented by the formula:

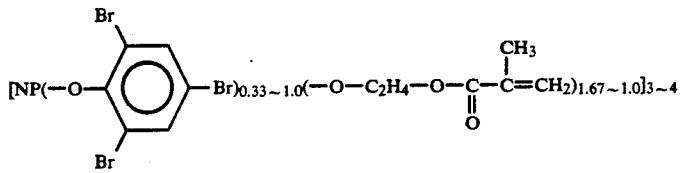

Cyclic compound represented by the formula:

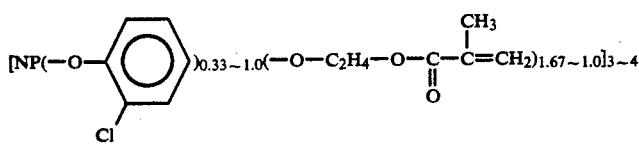

Cyclic compound represented by the formula:

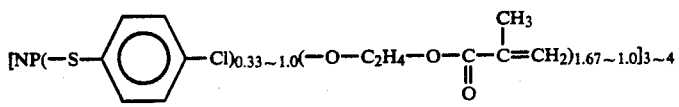

Cyclic compound represented by the formula:

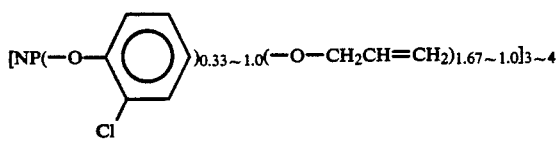

Such phosphazene compounds can be prepared by various methods. For example, when the group represented by the formula (II) is to be introduced as the substituent A, a hydroxyalkyl(meth)acrylate corresponding to the formula (II), i.e., the hydroxyalkyl (meth)acrylate represented by the formula:

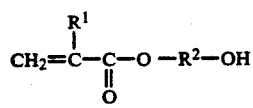

(wherein $R^1$ and $R^2$ have the same meanings as defined above) is used, when the group represented by the formula (III) is to be introduced as the substituent A, a hydroxyalkyl (meth)acrylate corresponding to the formula (III), i.e., the hydroxyalkyl (meth)acrylate represented by the formula:

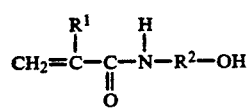

(wherein $R^1$ and $R^2$ have the same meanings as defined above) is used, and when the group represented by the formula (IV) is to be introduced as the substituent A, an allyl alcohol, allyl phenol, allyl ester of hydroxybenzoic acid or its derivative represented by the formula:

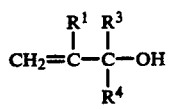

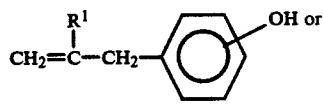

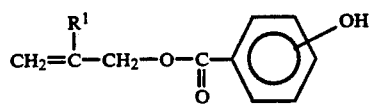

(wherein $R^1$, $R^3$ and $R^4$ have the same meanings as defined above) are used, respectively.

On the other hand, in the group represented by the formula (VIII) to be introduced as the substituent B, when M is an oxygen atom; an alkanol, a halogenated alkanol or its derivatives represented by the formula:

$R^5OH$ (wherein $R^5$ has the same meaning as defined above) is used. When M is a sulfur atom, an alkylmercaptane, a halogenated alkylmecaptane or its derivatives represented by the formula:

R⁵SH (wherein R⁵ has the same meaning as defined above) is used, and when M is an imide group, an alkylamine, a halogenated alkylamine or its derivatives represented by the formula:

R⁵NH₂

(wherein R⁵ has the same meaning as defined above) is used.

In addition, in the group represented by the formula (IX) to be introduced as the substituent B, when M is an oxygen atom, a phenol represented by the formula:

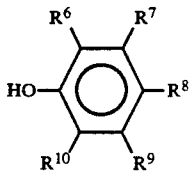

(wherein R⁶ to R¹⁰ have the same meanings as defined above) is used, and when M is a sulfur atom, a thiophenol represented by the formula:

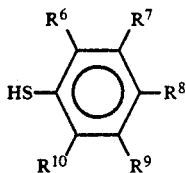

(wherein R⁶ to R¹⁰ have the same meanings as defined above) is used. When M is an imino group, aniline or its derivative represented by the formula:

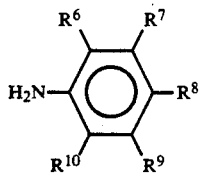

(wherein R⁶ to R¹⁰ have he same meanings as defined above) is used.

When the compound forming the substituent A and the compound forming the substituent B are reacted with chlorophosphazene (a cyclic compound represented by the formula (NPCl₂)ₙ or a chain compound represented by the formula Cl₄P.(NPCl₂)ₙ₋₁.NPCl₃, where n is three or more, preferably three to 18), the desired phosphezene compound of the formula (I) can be obtained.

When the compound forming the above substituent B is an alcohol, a mercaptane, a phenol or a thiophenol, it is preferred that these compounds are previously reacted with an alkali metal such as metal sodium or metal potassium for conversion into an alcoholate, a phenolate, a mercaptide or a thiophenolate.

To effect the reaction between the compounds forming the above substituents A and B with chlorophosphazene, a dehydrohalogenating agent such as a tertiary amine is preferably used. Examples of the tertiary amine may include trimethylamine, triethylamine, triisoprophlamine, tri-n-propylamine, tri-n-butylamine, pyridine and pycoline. Among them, pyridine is particularly preferred.

Furthermore, the reaction is usually carried out in an organic solvent. The organic solvents used may include benezene, toluene, xylene, chloroform, cyclohexane, methylene chloride, tetrahydrofuran, or 1,4-dioxane. They may be used singly or in combination.

The phosphazene compound which is main component of the hard coating layer to be formed on the surface of the molding material can be obtained by the reaction described above.

To form the hard coating layer on the surface of the molding material, a coating material is first prepared by compounding the above phosphazene compound and, if necessary, a mono-functional monomer and/or a polyfunctional monomer which are capable of copolymerizing with the phosphazene compound, and conventional additives for the hard coating layer. Then, the coating material is applied with the conventional coating such as roll-coating, spray coating onto the surface of the molding material, or dipping into the said coating material, and an active energy ray is irradiated or the coated material is heated to effect curing.

Examples of the mono-functional monomer and polyfunctional monomer that are capable of copolymerizing with the phosphazene compound may include compounds having reactive double bond(s) such as various compounds having acryloyl group, methacryloyl group, vinyl group or allyl group.

Additives may include an inorganic filler, an organic filler, an antistatic agent, or a UV-ray inhibitor, antioxidant.

Fine particle silica, alumina, glass, ceramics, etc. (which may be a solvent dispersed type) may be used as the inorganic filler.

The organic filler may also include fine particle acrylic resin, melamine resin, teflon resin, etc.

Furthermore, in order to form a heat resistant lubricating layer, a lubricant may be added.

The lubricant may be any phase of liquid, solid or grease, and a silicone type, fluorine type and other synthetic lubricant, or teflon fine particle, molybdenum disulfide, boron nitride, etc. may be used.

The coating material (coating solution) can be used by diluting it with an organic solvent for workability and controlling film thickness. Such organic solvents may include ketones such as methyl ethyl ketone and methyl isobutyl ketone; alcohols such as 2-propanol and 1-butanol; cellosolves; acetates; ethers; or aromatic hydrocarbons, singly or optionally in a combination thereof.

Irradiation of an active energy ray (visible ray, UV ray, electron beam, X-ray, γ-ray, etc.), heat curing or normal temperature curing are utilized for curing after coating.

When a curing method using visible ray or UV ray is utilized, a photo polymerization initiator (photosensitizer) is used. The polymerization initiator may be added to the coating solution. Examples of polymerization initiators may include 1-hydroxycyclohexylphenyl ketone, dibenzoyl, benzoyl, benzoin methyl ether, benzoin ethyl ether, p-chlorobenzophenone, p-methoxybonzophenone, benzoyl peroxide, di-t-butyl peroxide, Michler's ketone, and camphor quinone, and they may be used singly or in combination. Furthermore, 2-methyl [4-(methylthio)phenyl]-2-morpholino-1-propanone may be used.

When a heat curing or a normal temperature curing method is used, a peroxide compound and amine compound are used singly or in combination as the polymerization initiator. Examples of peroxide compounds may include benzoyl peroxide, p-chlorphenzoyl peroxide, 2,4-dichlorobenzoyl peroxide, t-butylhydro peroxide, di-t-butyl peroxide, dicumyl peroxide, t-butyl peroxiacetate, and t-butyl peroxibenzoate. Examples of amine compounds may include N,N-diethanol-p-toluidine, dimethyl-p-toluidine, p-toluidine, methyl-amine, t-butylamine, methylethlamine, diphenylamine, 4,4'-dinitrodiphenylamine, o-nitroamine, p-bromoaniline, or 2,4,6-tribromoaniline.

The amount of these compounds is not particularly limited, but when another functional material such as a photopolymerization initiator and a magnetic composition of the present invention is added to a layer mainly comprising the curable phosphazene compound, the total amount of the peroxide compound and the amine compound may usually be selected within the range of 0.05 to 5.0 parts by weight based on 100 parts by weight of the phosphazene compound.

An example of a coating agent to be formed on the hard coating layer of the present invention is shown below.

| | |
|---|---|
| (a) Phosphazene compound | 100 parts by weight |
| (b) Inorganic filler | 0 to 100 parts by weight |
| (c) Mono-functional monomer and/or poly-functional monomer capable of copolymerizing with the phosphazene compound | 0 to 100 parts by wieght |
| (d) Antistatic agent [based on 100 parts by weight of solid components of (a) to (c)] | 0 to 10 parts by weight |
| (e) Organic solvent | |
| (f) Photoinitiator or heat polymerization initiator [based on 100 parts by weight of solid components of (a) to (c)] | 0.5 to 5 parts by weight |

Furthermore, one example of a composition of the coating material to form a heat resistant lubricating layer on a base film of the present invention is shown below.

| | |
|---|---|
| (a) Phosphazene compound | 100 parts by weight |
| (b) Inorganic filler | 0 to 100 parts by weight |
| (c) Mono-functional monomer and/ or poly-functional monomer capable of copolymerizing with the phosphazene compound | 0 to 100 parts by weight |
| (d) Lubricating agent [based on 100 parts by weight of solid components of (a) to (c)] | 0 to 50 parts by weight |
| (e) Antistatic agent [based on 100 parts by weight of solid components of (a) to (c)] | 0 to 10 parts by weight |
| (f) Organic solvent | |
| (g) Photoinitiator or heat polymerization initiator [based on 100 parts by weight of solid components of (a) to (c)] | 0.05 to 5 parts by weight |

Organic solvents may not necessarily be used, but in view of workability and controlling film thickness after curing as mentioned above, the above materials are preferably dissolved in an organic solvent with a concentration of 0.5 to 60% by weight.

In the present invention, the hard coating layer is usually prepared with a thickness of 0.01 to 1000 $\mu$m. If it is less than 0.01 $\mu$m, its mechanical strength is insufficient, and if it exceeds 1000 $\mu$m, flexibility is sometimes poor.

The styrene-based resin composite material of the present invention is prepared as mentioned above.

The ink ribbon in the present invention is that prepared by providing, on a base film comprising the above styrene-based polymer or its composition, the above heat resistant lubricating layer, and also providing an ink layer at the opposite side thereto. The heat resistant lubricating layer may be formed after providing the ink layer on the base film or before providing the ink layer. However, in view of workability, the method in which the ink layer is provided after forming the heat resistant lubricating layer is formed is preferred.

To form the heat resistant lubricating layer, the coating material prepared by the method mentioned above is applied on one surface (back surface, a surface opposite to the ink layer) of a base film for a desired ink ribbon by the conventionally known coating method such as the spinner method, the spray method, or the roll coater method, and then, after removing a solvent when the solvent is used, a curable compound is cured by normal temperature curing, heat curing or irradiation of UV ray, electron beam, X-ray, $\gamma$-ray, etc. Among these curing methods, the curing method using UV rays is preferred, and in this case, it is preferred to irradiate UV rays having a wavelength in the range of 200 to 50 nm for 0.1 second or more, preferably from 0.3 to 30 seconds.

The integrating dose of irradiated ray at this time is usually 60 to 5000 mJ/cm$^2$. If the heat curing method is employed, it is preferred to carry out complete curing at a temperature of 100° C. or higher.

The thickness of the heat resistant lubricating layer is preferably in the range of 0.03 to 20 $\mu$m, but the range of 0.05 to 10 $\mu$m is more preferred in view of the balance between the heat resistant lubricating effect and ease of use of the ink ribbon.

The heat resistant lubricating layer thus obtained has remarkably excellent adhesiveness to the base film, and yet also has excellent mechanical, thermal and chemical properties whereby adhesion resistance, lubricating property, heat resistance, durability, running property and mar resistance of the ink ribbon can be remarkably improved.

The magnetic recording medium of the present invention is a material compounded a magnetic composition (magnetic paint) to the styrene-based resin film with the curable phosphazene compound which corresponds to the hard coating layer as a binder. The magnetic recording medium may be prepared by the conventional method. More specifically, to 100 parts by weight of magnetic materials such as iron, oxides ($\gamma$-iron oxide, tri-iron tetroxide, etc.), cobalt-containing $\gamma$-iron oxide, chromium oxides, pure iron, iron-based alloy (cobalt-iron-nickel alloy, etc.) or nickel-cobalt alloys, are added 10 to 50 parts by weight of the above binder and 100 to 300 parts by weight of a suitable solvent (diluent) such as benzene, toluene, methyl ethyl ketone, cyclohexanone, alcohol, and if necessary, further adding two to 15 parts by weight of an antistatic agent, two to 15 parts by weight of a lubricating agent, two to seven parts by weight of an abrasive agent and five to 10 parts by weight of a dispersant, and the resulting mixture is kneaded sufficiently with a ball mill etc. Then, the resulting magnetic composition (magnetic paint) is applied on the support (film, tape, card, disc, etc.) and is irradiated with an active energy ray (UV ray, visible ray, electron beam, X-ray, γ-ray. etc.) or heating to cure the composition to form a magnetic layer.

Furthermore, in the above magnetic composition, other curable compound may be included through a reaction. The curable compound obtained by the reaction may include methyl acrylate, hydroxyethyl acrylate, ethylene glycol diacrylate, diethylene glycol diacrylate, a mixture of triethylene glycol diacrylate, tetraethylene glycol diacrylate and methacrylate, glycidyl acrylate, 2,2'-bis(acryloyloxyphenyl)propane, 2,2'-bis[4-(3-methacryloyloxy)-2-hydroxy-prppoxyphenyl]propane, vinyl esters of carboxylic acid (vinyl acetate, vinyl stearate, etc.) and ethylene-based unsaturated dicarboxylic acids (fumalic acid, maleic acid, maleic anhydride, itaconic acid, itaconic anhydride, etc.).

The magnetic recording medium of the present invention thus obtained has various merits such as excellent heat resistance, and good adhesiveness between the magnetic layer and the support, etc. A back coating layer and a magnetic over coated layer may be provided for the magnetic recording medium using phosphazene compound.

As mentioned above, according to the present invention, a composite material that is very hard, excellent in adhesiveness to the support and a coating film that peels with difficulty can be obtained.

Consequently, the composite material of the present invention can be effectively utilized for various molding materials having a coating film with excellent physical properties such as hardness, weather resistance, heat resistance, solvent resistance, and chemical resistance and lublicity, for example, construction materials, and automotive parts.

In addition, the ink ribbon of the present invention shows remarkably excellent heat resistance and characteristics such as adhesiveness and running properties.

The ink ribbon of the present invention, then, can be effectively utilized as an ink ribbon for a printer of various information machines and communicating machines such as wordprocessors, personal computers and bar coded printer, facsimile and colored hard copy.

Furthermore, by providing a magnetic layer formed by compounding a curable phosphazene compound to a magnetic material on a support comprising a styrene-based polymer mainly having a syndiotactic configuration, a magnetic recording medium which has strong adhesiveness with a support, high tensional modulus of elasticity, excellent heat resistance, abrasion resistance and solvent resistance, and also excellent in dispersibility of the magnetic component can be obtained.

The magnetic recording medium of the present invention, then, has a long life and excellent properties of running stability, S/N ratio, etc.

Therefore, the magnetic recording medium of the present invention can be widely and effectively utilized for various electronics and magnetic recording materials.

Reference example 1

(Preparation of polystyrene (SPS) having syndiotactic configuration)

Two liters of toluene as a solvent, 1 mmole of cyclopentadienyl titanium trichloride and 0.8 mole of methylaluminoxane in terms of aluminum atom as catalysts were charged into a reactor and 3.6 liters of styrene was added thereto at 20° C., and the polymerization reaction was carried out for one hour.

After completion of the reaction, the product was washed with a mixture of hydrochloric acid and methanol to decompose and remove the catalyst components, and then the product was dried to give 330 g of a styrene-based polymer (polystyrene; SPS). Next, this polymer was subjected to Soxhlet extraction using methyl ethyl ketone as a solvent to give an extract residue of 95% by weight. The weight average molecular weight of the product was 290,000, the number average molecular weight was 158,000 and the melting point was 270° C.. The NMR spectral analysis of the said polymer using a carbon isotope ($^{13}$C-NMR, solvent: 1,2-dichlorobenzene) showed a signal at 145.35 ppm, which was ascribable to the syndiotactic configuration, and the syndiotacticity in terms of racemic pentad as calculated from the peak area was 96%.

Reference example 2 ( preparation of a molding material comprising SPS)

To SPS obtained by the above Reference example 1 were mixed each 0.1 part by weight of bis (2,4-di-t-butylphenyl)-pentaerythrytol diphosphite and tetrakis[-methylele (3,5-di-t-butyl-4-hydroxyhydrocinnamate)] methane as antioxidants and the mixture was extruded from a twin-screw extruder to prepare pellets.

The resulting pellets were supplied to an apparatus to which a T-die was attached at the top of a single-screw extruder, and extrusion was carried out with a cylinder temperature of 300° C. and a T-die temperature of 310° C. to prepare a sheet with a thickness of 1300 μm. At this time, the cooling roller for the sheet has a surface temperature of 30° C.

The raw sheet (original sheet) for stretching thus obtained was transparent and had a density of 1.04 g/m$^3$, a glass transition temperature of 100° C. and a crystallinity of 12%.

Next, the sheet was subjected to simultaneous biaxial stretching with a draw ratio of 2.5 times in each direction and at a stretching temperature of 120° C. The resulting stretched film was annealed with fixed ends thereof at 250° C. for 30 seconds. The thickness of the film at this time was 200 μm.

Reference example 3

(Molding of a SPS plate having a thickness of 3 mm)

Using the pellets prepared in Reference example 2, injection molding was carried out using an injection molding machine at a melting temperature of 290° C. and a mold temperature of 150° C. to give a plate with a thickness of 3 mm. This plate had a crystallinity of 49%.

Preparation example 1

Preparation of curable phosphazene compound (A)

Into a 2-liter flask was dissolved 86.8 g of hexachlorocyclo triphosphazene (cyclic compound of the formula (NPCl$_2$)$_3$) in 338 g of dehydrated benzene. To the benzene solution were added 110 g of sodium carbonate, 155 g of pyridine and 0.23 g of hydroquinone, and the resulting mixture was stirred.

Two-hundred ml of 2-hydroxyethyl methacrylate was dissolved separately in 237 ml of benzene and the resulting solution was added dropwise into the flask and the reaction was carried out at 50° C. for 8 hours. After the mixture was allowed to stand at room temperature for 15 hours, it was filtered to remove hydrochloride of pyridine and sodium carbonate.

The filtrate was washed with water, dried using Glauber's salt (sodium sulfate) and the solvent was removed under a reduced pressure to give 200 g (Yield: 88.3%) of viscous 1,1,3,3,5,5-hexa (methacryloylethylenedioxy) cyclotriphosphazene represented by the following formula:

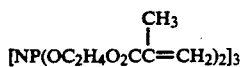

$$[NP(OC_2H_4O_2CC=CH_2)_2]_3$$

Preparation example 2

Preparation of curable phosphazene compound (B)

Into a 2-liter flask equipped with a thermometer, a stirrer, a dropping funnel and a condenser, were charged 100 ml of tetrahydrofuran and 25.5 g of metallic sodium. To the reacting solution was added dropwise 104 g (1.11 mole) of phenol, after which the mixture was refluxed for 3 hours to give phenolate.

Next, 198 g (0.555 mole) of a hexachlorocyclotriphosphazene solution was dissolved in 400 ml of benzene added dropwise to the above tetrahydrofuran solution containing the phenolate. Thereafter, the reaction proceeded under reflux for 4 hours.

Then, the temperature of the reaction mixture was returned to room temperature, and 352 g (4.45 mole) of pyridine was added thereto. Furthermore, 381 g (2.45 mole) of 2-hydroxyethyl methacrylate was gradually added dropwise from the dropping funnel and the reaction was carried out at 60° C. for 20 hours. Then, the precipitated solid was filtered off and the solvent in the resulting filtrate was removed under reduced pressure, and the residue was sufficiently dried to give 452 g of a yellow liquid material.

Examples 1 and 2

To the curable phosphazene compound (A) was added a mixed solvent of isopropyl alcohol and methyl ethyl ketone (1:1 weight ratio), and it was adjusted to have a viscosity of 10 cP. Three parts by weight of 1-hydroxycyclohexyl phenyl ketone (produced by Ciba Geigy AG) was added to the above curable compound as a photoinitiator. After being dissolved, it was coated by bar coater (No. 20) onto a SPS resin molding material (a film having a thickness of 200 μm and a plate having a thickness of 3 mm) produced in Reference examples 2 and 3 and UV rays were irradiated to give an integrated dose of 500 mJ/cm$^2$ to produce coated films having a thickness of 6 μm.

Examples 3 and 4

In the same manner as in Example 1 except that the curable phosphazene compound (A) used in Example 1 was replaced with curable phosphazene compound (B), coated films having a thickness of 6 μm were obtained.

Comparative example 1

The 3 mm thick SPS plate prepared in Reference example 3 was used as it was.

Comparative example 2

Using a commercially available acryl-based coating material, a coated film having a thickness of 6 μm was obtained in the same manner as in Example 1.

The evaluated results of the films obtained in Examples 1 to 4 and Comparative examples 1 and 2 are shown in Table 1 and the conditions for evaluation and standard for judgement are shown in Table 2.

TABLE 1

|  | Example 1 | | Example 2 | | Example 3 | | Example 4 | | Comparative example 1 | Comparative example 2 | |
| --- | --- | --- | --- | --- | --- | --- | --- | --- | --- | --- | --- |
| Taber abrasion | 8% | | 10% | | 8% | | 10% | | 38% | 28% | |
| Sand abrasion | 12% | | 13% | | 12% | | 13% | | 46% | 38% | |
| Weather resistance | No*[1] | 100/100 | No*[1] | 100/100 | No*[1] | 100/100 | No*[1] | 100/100 | No*[2] | 2500 hrs, crack occurred, peel off. | |
| Initial adhesiveness | — | 100/100 | — | 100/100 | — | 100/100 | — | 100/100 | No*[2] | — | 20/100 |
| Heat resistance | No*[1] | 100/100 | No*[1] | 100/100 | No*[1] | 100/100 | No*[1] | 100/100 | No*[2] | No*[1] | 20/100 |
| Heat shock | No*[1] | 100/100 | No*[1] | 100/100 | No*[1] | 100/100 | No*[1] | 100/100 | No*[2] | Partially peeled | — |
| Hot water resistance | No*[1] | 100/100 | No*[1] | 100/100 | No*[1] | 100/100 | No*[1] | 100/100 | No*[2] | Crack occurred | 10/100 |
| Humidity resistance | No*[1] | 100/100 | No*[1] | 100/100 | No*[1] | 100/100 | No*[1] | 100/100 | No*[2] | No*[1] | 10/100 |
| Acid resistance | No*[1] | 100/100 | No*[1] | 100/100 | No*[1] | 100/100 | No*[1] | 100/100 | No*[2] | No*[1] | 20/100 |
| Alkali resistance | No*[1] | 100/100 | No*[1] | 100/100 | No*[1] | 100/100 | No*[1] | 100/100 | No*[2] | No*[1] | 20/100 |

*[1]No change in appearance of the film
*[2]No change in appearance

TABLE 2

| Evaluation | Evaluation conditions | Judgement |
| --- | --- | --- |
| Taper abrasion | Sample disc rotation number: 100 rotations, truck wheel: CS-10 (500 g). | Difference of haze before and after the test |

TABLE 2-continued

| Evaluation | Evaluation conditions | Judgement |
|---|---|---|
| Sand abrasion | Inclination angle of sample: 45°, Amount of No. 60 carborundum used: 1000 g, Drop height: 50 cm | Difference of haze before and after the test |
| Weather resistance | S.W.M. B.P.T.: 63° C., Humidity: 50% RH, Rainfall cycle: 12 min/60 min, Time: 2500 hrs. | Observed visually, Cross-cut peeling with cellophane tape (100/100 No peeling. 0/100 Completely peeled) |
| Initial adhesion | Cross-cut peeling with cellophane tape | Cross-cut.peeled with cellophane tape |
| Heat resistance | 120° C. × 500 hrs. | Observed visually, Cross-cut peeled with cellophane tape |
| Heat shock | −50° C., 100° C., 50 cycles as 1 cycle for 2 hrs. | Observed visually, Cross-cut peeled with cellophane tape |
| Hot water resistance | Cross-cut sample was dipped in 90° C. water for 3 hrs. | Observed visually, Cross-cut peeled with cellphane tape |
| Humidity resistance | Humidity: 98%, Temperature: 50° C., Time: 500 hrs. | Observed visually, Cross-cut peeled with cellophane tape |
| Acid resistance | Sample was dipped into 5% HCl solution for 48 hrs. | Observed visually, Cross-cut peeled with cellophane tape |
| Alkali resistance | Sample was dipped into 5% NaOH solution for 48 hrs. | Observed visually, Cross-cut peeled with cellophane tape |

Reference example 4

(Preparation of molding material comprising SPS)

In the same manner as in Reference example 2 except that the raw sheet for stretching was stretched with a draw ratio of 4 times in the both directions when stretching, a film having a thickness of 4 μm was obtained.

Example 5

(An ink coated film)

Fifteen parts by weight of toluene, 6 parts by weight of ethylene-vinyl acetate copolymer and 2 parts by weight of carbon black were mixed and shaken in a vibrating ball mill for 3 hours to prepare an ink for an ink ribbon.

Next, the ink was coated onto a styrene-based polymer stretched film having a thickness of 4 μm with a coating layer thickness of 4 μm using a roll coater to give an ink-coated film.

Example 6

(Ink ribbon with heat resistant lubricating layer)

A curable phosphazene (A) was dissolved in methyl isobutyl ketone, and 3 parts by weight of 1-hydroxycyclohexylphenyl ketone (photo initiator), 10 parts by weight of a cross linked polymer fine powder of methyl methacrylatedivinyl benzene and 0.3 parts by weight of silicone polyether copolymer were added to the solution and dissolved or dispersed to prepare a coating material for the heat resistant lubricating layer.

Next, on SPS film of 4 μm thickness which was prepared in Reference example 4 was coated the coating material for the heat resistant lubricating layer with a roll coater and removed a solvent at 80° C., it was irradiated with UV rays with an integrated dose of 1500 mJ/cm² and then coated a heat resistant lubricating layer with a film thickness of 0.8 μm. Successively, an ink was coated on the surface of an opposite side of the heat resistant lubricating layer with the same manner prepared in Example 5 and an ink ribbon was prepared.

Example 7

(Ink ribbon with heat resistant lubricating layer)

A commercially available silicone-based coating material was diluted with toluene to prepare a coating material for the heat resistant lubricating layer. On SPS film of 4 μm thickness which was prepared in Reference example 4 was coated the above coating material for the heat resistant lubricating layer with a roll coater and dried at 90° C. for 10 minutes to prepare a film having a heat resistant lubricating layer with a thickness of 0.8 μm.

Next, an ink was coated on the surface of an opposite side of the heat resistant lubricating layer in the same manner as described in Example 5 and an ink ribbons were obtained.

Comparative examples 3 and 4

By using a commercially available film made of a polyester (film thickness 5.8 μm), an ink-coated film having an ink layer with a thickness of 4 μm was obtained in the same manner as described in Example 5.

Coating with the coating material for the heat resistant lubricating layer used in Example 6 and Example 7 with the coating material for the heat resistant lubricating layer used in Example 6 and Example 7, by using a commercially available film made of a polyester (film thickness 5.8 μm), films having a heat resistant lubricating layer with a thickness of 0.8 μm were obtained.

Next, an ink-coated film having an ink layer with a thickness of 4 μm on the surface of the opposite side to the heat resistant lubricating layer was obtained in the same manner as described in Example 5.

The evaluated results of the ink ribbons obtained in Examples 6 and 7 and Comparative examples 3 and 4 are shown in Table 3.

The experiments were carried out by the following methods.

1) Adhesiveness

Cellophane tape was attached to one side of a heat resistant lubricating layer and after being torn off strongly, the adhesiveness of the heat resistant lubricating layer to an ink ribbon base film was observed.

2) Running property

A sample was wound in a roll state, and running property, change in speed and meandering characteristics were evaluated, by using the commercially available bar code printer.

3) Heat resistance

Using a thermal head, of the commercially available bar code printer printing was carried out at the same position repeatedly and the state of the support film was evaluated.

50 times or more: No deterioration of the support film was observed after printing 50 times.

30 times or less: Crease and break were observed on the support film after printing 10 to 30 times.

TABLE 3

|  | Example 6 | Example 7 | Comparative example 3 | Comparative example 4 |
|---|---|---|---|---|
| Adhesiveness | Good | Good | Good | Partially peeled off |
| Running property | Good | Good | Good | Good |
| Heat resistance | 50 times or more | 50 times or more | 50 times or more | 30 times or less |

Reference example 5

In the same manner as in Reference example 2, except that the raw sheet was stretched with a draw ratio of 3.5 times in the both directions, and a film having a thickness of 20 μm was obtained.

Example 8

A mixture of 400 parts by weight of γiron oxide (γ-Fe₂O₃) powder, 150 parts by weight of the phosphazene compound obtained in Preparation example 1, 4 parts by weight of carbon black, 10 parts by weight of a silicone oil, 6 parts by weight of recitin, 450 parts by weight of methyl ethyl ketone and 450 parts by weight of toluene were kneaded in a ball mill for 50 hours to give a magnetic composition. This composition was coated onto a 20 μm thick SPS film obtained in Reference example 5 in order to have a dried film thickness of 5 μm to form a magnetic layer.

Next, after drying at 90° C., and electron beam having an irradiation dose of 200 keV and 6 Mrad was irradiated to cure the magnetic layer to prepare a magnetic recording medium.

Various physical properties of the resulting magnetic recording media were measured. The results are shown in Table 4.

Comparative example 5

In the same manner as in Example 8, except that a polyethyleneterephthalate film with a thickness of 20 μm was used instead of the SPS film in Example 8, and a magnetic recording medium was obtained.

Measured results of various physical properties are shown in Table 4.

Comparative example 6

(1) A polyester diol (a number average molecular weight of 2500 and OH value of 48.3) was obtained using 1,4-butane-diol and adipic acid as starting materials, and it was converted into a urethane polymer by reacting with tolylene diisocyanate. Then, 2-hydroxyethyl acrylate was further reacted to the resulting material to give a polymer (a number average molecular weight of 28000).

(2) The same procedures were conducted as in Example 8 except that the polymer obtained in (1) above was used instead of the phosphazene compound of Preparation example 1. The results are shown in Table 4.

TABLE 4

| No. | Adhesiveness*¹ of substrate film and magnetic layer | Solvent*² resistance (time) | Abrasion*³ resistance (mg) | Dispersibility*⁴ | Heat*⁵ resistance | Tensile modulus elasticity (kg/cm) |
|---|---|---|---|---|---|---|
| Example 8 | ○ | 250 or more | 0.2 | ⊙ | ○ | 55,000 |
| Comparative example 5 | ○ | 250 or more | 0.1 | ⊙ | X | 40,000 |
| Comparative example 6 | Δ | 80 | 0.8 | ○ | ○ | 40,000 |

*¹After attaching cellophane tape to the surface of a tape, the state when it was torn off strongly as above was evaluated.
○ ... Not torn off, Δ ... Partially torn off.
*²The film surface was rubbed with a gauze soaked in methyl ethyl ketone and was evaluated each time until a support revealed.
*³According to JIS K 7204, a surface was rubbed with a truck wheel and was evaluated by the weight difference before and after the treatment.
*⁴The surface condition of a magnetic layer was observed using a scanning-type electron microscope with 2000-magnification.
⊙ ... Markedly good, ○ ... Good.
*⁵The condition after being allowed to stand under conditions with a temperature of 80° C. and humidity of 80% for 5000 hours was observed.
○ ... No stretching, wrinkles or shrinkage.
X ... Stretching and shrinkage are present.

What is claimed is:

1. An ink ribbon which comprises a stretched base film consisting essentially of a styrene-based polymer having a syndiotactic configuration, an ink layer formed on the base film and a heat resistant lubricating layer consisting essentially of a curable phosphazene compound formed on the base film at the opposite side to the ink layer.

2. An ink ribbon according to claim 1, wherein the phosphazene compound is a chain compound having a recurring unit represented by the formula:

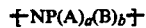

wherein a and b each represent a real number satisfying a>0, b≧0 and a+b=2; A represents a group that can be cured by polymerization, and B represents a group that cannot be cured by polymerization; and having a polymerization degree of 3 or more.

3. An ink ribbon according to claim 1, wherein the phosphazene compound is a cyclic compound having a recurring unit represented by the formula:

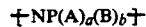

wherein a and b each represent a real number satisfying a>0, b≧0 and a+b=2; A represents a group that can be cured by polymerization, and B represents a group that cannot be cured by polymerization.

4. The ink ribbon of claim 1, wherein the phosphazene compound is a cyclic compound represented by the formula
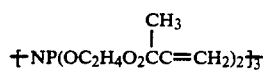
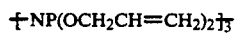
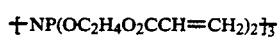
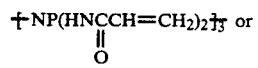
5. The ink ribbon of claim 1, wherein the phosphazene compound is a cyclic compound represented by the formula
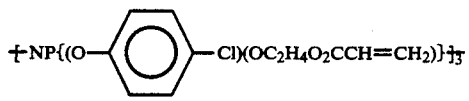
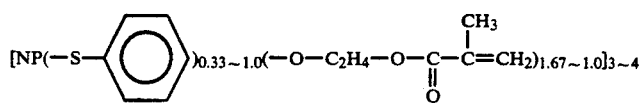
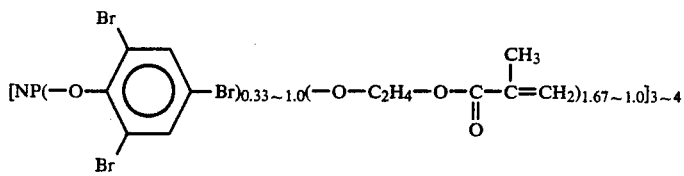
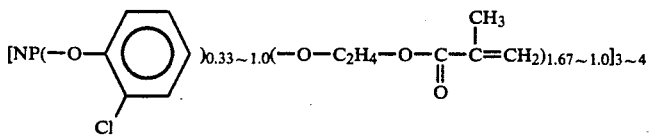
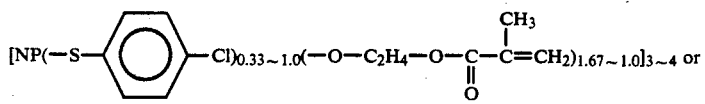
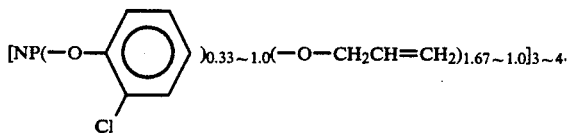

UNITED STATES PATENT AND TRADEMARK OFFICE
CERTIFICATE OF CORRECTION

PATENT NO. : 5,082,717

DATED : January 21, 1992

INVENTOR(S) : YAGUCHI et al

It is certified that error appears in the above-identified patent and that said Letters Patent is hereby corrected as shown below:

```
Title Page, [56] References Cited, under "FOREIGN PATENT
DOCUMENTS" insert  -- 2 046 627  11/1980  Great Britain --.
```

Signed and Sealed this

Sixth Day of September, 1994

Attest:

BRUCE LEHMAN

Attesting Officer

Commissioner of Patents and Trademarks